United States Patent [19]

Bright et al.

[11] Patent Number: 5,466,610
[45] Date of Patent: Nov. 14, 1995

[54] IMMUNOASSAYS FOR INSULIN SENSITIVITY ENHANCERS, INSULIN SENSITIVITY ENHANCER ANTIBODIES, AND NON-THIAZOLIDINEDIONE INSULIN SENSITIVITY ENHANCER COMPOSITIONS

[75] Inventors: Stuart W. Bright; Gerald Gold; Scott W. Sage, all of Indianapolis, Ind.; John R. Sportsman, Palo Alto, Calif.

[73] Assignee: Eli Lilly and Company, Indianapolis, Ind.

[21] Appl. No.: 117,447

[22] Filed: Sep. 7, 1993

[51] Int. Cl.$^6$ .................. G01N 33/577; C07K 16/44
[52] U.S. Cl. .................. 436/518; 436/531; 436/532; 436/533; 436/534; 436/546; 436/548; 436/815; 530/388.9
[58] Field of Search .................. 530/388.9, 389.8; 436/518, 531, 532, 533, 534, 546, 548, 815

[56] References Cited

U.S. PATENT DOCUMENTS

| | | |
|---|---|---|
| 3,684,754 | 8/1972 | Barie, Jr. et al. |
| 5,296,605 | 3/1994 | de Nanteuil et al. .................. 546/176 |

OTHER PUBLICATIONS

Y. Iwamoto et al., Diabetes Care, vol. 14, No. 11, pp. 1083–1086 (1991).
G. Galfre et al., Methods in Immunology, vol. 73, pp. 3–46 (1981), Academic Press, Inc.
J. Gosling, Clin. Chem., vol. 36, No. 8, pp. 1408–1427 (1990).
Bowen, et al., *Metabolism*, 40 (10), 1025–1030 (1991).
Chang, et al., *Pathogenesis and New Approaches to the Study of Noninsulin–Dependent Diabetes Mellitus*, Alan R. Liss, Inc., 177–192 (1988).
Ciaraldi, et al., *Metabolism*, 39 (10), 1056–62 (1990).
Colca, et al., *Diabetes*, 40, 1669–1674, (1991).
Couraud, et al., *J. Biol. Chem.*, 260 (16), 9461–9469 (1985).
Couraud, *J. Immunol.*, 136 (9), 3365–3370 (1986).
Duce, et al., *Biochem. Soc. Trans.*, 19, 143–146 (1991).
Depla, et al., *Molecular Immun.*, 28 (7), 743–751 (1991).
Dontenwill, et al., *Life Sciences*, 50, 1859–1868 (1992).
Fujiwara, et al., *Metabolism*, 40 (11), 1213–18 (1991).
Garcia, et al., *Science*, 257, 528–531 (1992).
Gardner, et al., *J. Endocrinology*, 123, 53–59 (1990).
Glasel, et al., *Molecular Immunol.*, 20 (12), 1419–1422 (1983).
Glasel, et al., *Biochem. and Biophys. Research Comm.*, 136 (3), 1177–1184 (1986).
Guillet, et al., *Proc. Natl. Acad. Sci. USA*, 82, 1781–1784 (1985).
Homcy, et al., *J. Clin. Invest.*, 69, 1147–1154 (1982).
Ikeda, et al., *Arzneimittel Forschung/Drug Research*, 40 (1), 156–162 (1990).
Islam, et al., *Eur. J. Immunol.*, 13, 57–63 (1983).
Kussie, et al., *Meth. in Enzymol.*, 178, 49–63 (1989).
Kussie et al., *J. Immunol.*, 146 (12), 4248–4257 (1991).
Lykkeg rd, *Acta path. Microbiol. Scand.*, 88, 179–185 (1980).
Galfre, et al., *Meth. Enzymol.*, 73, 3–46 (1981).
Mons, et al., *J. Hirnforsch*, 32 (5), 617–625 (1991).
Mor, et al., *Endocrinology*, 130 (6), 3633–3640 (1992).
Ng, et al., *Biochem. Pharmacology*, 34 (16), 2853–2858 (1985).
Noseworthy, et al., *J. Immunol.*, 131 (5), 2533–2538 (1983).
Sawutz, et al., *J. Immunol.*, 135 (4), 2713–2718 (1985).
Schreiber, et al., *Proc. Natl. Acad. Sci. USA*, 77 (12), 7385–7389 (1980).
Sege, et al., *Proc. Natl. Acad. Sci. USA*, 75 (5), 2443–2447 (1978).
Strosberg, *Meth. in Enzymol.*, 178, 179–190 (1989).
Taber, et al., *Clinical Chem.*, 37 (2), 254–260 (1991).
Tamir, et al., *J. Neurochem.*, 57 (3), 930–942 (1991).
Tassi, et al., *Immunol. Lett.*, 27, 39–44 (1991).
Vaux, et al., *Methods in Cell Biology*, Academic Press, Inc., vol. 34, 1–38 (1991).
Wassermann, et al., *Proc. Natl. Acad. Sci. USA*, 79, 4810–4814 (1982).
Wolff, et al., *Med. Chem. Res.*, 1, 101–108 (1991).
Zenke, et al., *Molecular Immunol.*, 29 (3), 343–351 (1992).

*Primary Examiner*—Mary E. Ceperley
*Attorney, Agent, or Firm*—Merchant, Gould, Smith, Edell, Welter & Schmidt

[57] ABSTRACT

Methods have been developed to produce novel compounds by covalently coupling thiazolidinedione insulin sensitivity enhancers (ISEs) to proteins. These novel compounds are well suited for producing antibodies, which are specific for thiazolidinedione ISEs and which are well suited for fluorescent immunoassays of thiazolidinedione and non-thiazolidinedione ISEs in buffers and biological tissues. Antibodies also are well suited for high-volume screening for immunologically related novel, non-thiazolidinedione and thiazolidinedione ISEs.

7 Claims, 5 Drawing Sheets

IMMUNOASSAYS FOR INSULIN SENSITIVITY ENHANCERS, INSULIN SENSITIVITY ENHANCER ANTIBODIES, AND NON-THIAZOLIDINEDIONE INSULIN SENSITIVITY ENHANCER COMPOSITIONS

TECHNICAL FIELD

The present invention relates to methods for the preparation of antibodies, monoclonal antibodies, and anti-idiotype antibodies against thiazolidinedione insulin sensitivity enhancers (ISEs), and for their use in fluorescent immunoassays and in high-volume screens for novel, non-thiazolidinedione and thiazolidinedione ISEs. The present invention also provides for novel thiazolidinedione ISE antibodies, anti-idiotype antibodies, and non-thiazolidinedione ISEs.

BACKGROUND OF THE INVENTION

Type II, non-insulin dependent, diabetes mellitus is characterized by endocrine abnormalities in pancreatic islets (insufficient insulin release) combined with enhanced glucagon release, as well as metabolic abnormalities in several target tissues of insulin (resistance to insulin's effects on glucose and lipid metabolism in muscle).

Current anti-diabetic therapies, such as sulfonylureas and insulin, partially correct the endocrine abnormalities associated with type II diabetes by either enhancing or supplementing the deficient, endogenous insulin secretion. These compounds have little, if any, ability to attenuate the associated insulin resistance in these individuals. Another structural class of compounds, thiazolidinediones, also has been demonstrated to lower blood glucose, insulin levels, and lipid levels in several animal models of type II diabetes. Because thiazolidinediones lower, rather than raise, insulin levels, they appear to have a different mechanism of action than either insulin or sulfonylureas and, thus, they have been termed insulin sensitivity enhancers (ISEs).

Unfortunately, thiazolidinedione ISEs also have been associated with weight gain, anemia, and cardiac hypertrophy. These unwanted side effects have slowed the development of thiazolidinedione ISEs for therapy for type II diabetes. The search for new classes of compounds that lower glucose, insulin and lipid levels via the same molecular mechanism as thiazolidinedione ISEs has been hampered by the fact that the molecular mechanism of thiazolidinedione ISEs remains unknown despite the numerous reports documenting that they have profound effects on glucose and/or lipid metabolism in liver, muscle and fat. Thus, the search for non-thiazolidinedione ISEs would greatly be facilitated by elucidation of a molecular mechanism for thiazolidinedione ISEs or by development of a screening procedure that could identify novel classes of compounds, which could trigger the same molecular mechanism as thiazolidinedione ISEs.

SUMMARY OF THE INVENTION

The present invention relates to a method for detecting non-thiazolidinedione and thiazolidinedione insulin sensitivity enhancer compounds using a fluorescent immunoassay. For the assay, a sample is provided containing a non-thiazolidinedione or thiazolidinedione compound suspected to have thiazolidinedione-like insulin sensitivity enhancer (ISE) activity. The sample is incubated with a first antibody to a thiazolidinedione ISE and a substrate-bound second antibody conjugate to form a complex of first antibody with the non-thiazolidinedione or thiazolidinedione ISE which is bound to the second antibody conjugate. Following incubation, a labeled thiazolidinedione ISE conjugate is added to the sample. Preferably, the conjugate employs a fluorescent label. The labeled thiazolidinedione ISE forms a complex with the first antibody which is bound to the second antibody conjugate. Following a selected reaction period, the amount of labeled thiazolidinedione ISE first antibody complex bound with the second antibody conjugate is measured to detect the presence and/or quantify the amount of non-thiazolidinedione or thiazolidinedione ISE in the sample.

The phycobiliproteins exemplify preferred fluorescent labels for use in the present invention. One such useful phycobiliprotein is β-phycoerythrin. Further, in a preferred embodiment, the fluorescent label contains an intact thiazolidinedione ISE, such as the succinyl CS-045 conjugate of β-phycoerythrin, or a fragment of a thiazolidinedione ISE, such as the succinyl LY 301318 conjugate of β-phycoerythrin.

The present invention also provides a method for selecting a monoclonal antibody with specific binding activity to a thiazolidinedione ISE compound. The antibody is selected by first administering a thiazolidinedione ISE immunogen to an animal. After a suitable period of time, spleen cells are harvested from an animal exhibiting an elevated antibody titer to the thiazolidinedione ISE immunogen. Hybridomas are then prepared to provide monoclonal antibodies that bind to a labeled protein thiazolidinedione ISE conjugate. These monoclonal antibodies are then screened for binding activity to a plurality of chosen thiazolidinedione ISEs. A monoclonal antibody exhibiting high binding affinity to each of the chosen thiazolidinedione ISEs employed in screening the monoclonal antibodies is then selected.

Preferred immunogens for selecting antibodies with specific binding affinity to thiazolidinedione ISE compounds include CS-045 and LY 301318 immunogens. A preferred set of thiazolidinedione ISEs for screening monoclonal antibodies include CS-045, LY 282449, and ciglitazone.

The present invention also provides for monoclonal antibodies having specific binding affinity to thiazolidinedione ISE compounds and non-thiazolidinedione ISE compounds that exhibit thiazolidinedione ISE bioactivity or immunological reactivity. A preferred monoclonal antibody is produced by hybridoma cell line 13E3.

Monoclonal antibodies can also be employed to produce anti-idiotypic antibodies useful for further evaluation of a thiazolidinedione ISE receptor. Two preferred anti-idiotype antibodies are produced by hybridoma cell lines 7E7 and 2E5.

The present invention also can be used to identify new, non-thiazolidinedione ISE compounds. One such compound has been designated LY 116196.

The method of the present invention is also useful for monitoring blood levels of type II anti-diabetic thiazolidinedione and/or non-thiazolidinedione ISE compounds.

DETAILED DESCRIPTION OF THE INVENTION

As used herein, the term "thiazolidinedione insulin sensitivity enhancer (ISE)" refers to a class of thiazole ring-containing compounds that exhibit type II anti-diabetic activity, including lowering of blood glucose, insulin levels, and lipid levels in animals with type II diabetes. The term "non-thiazolidinedione 'insulin sensitivity enhancer' (ISE)" refers to a group of compounds that lack the thiazole ring but share common immunologic structural features with the above-named thiazolidinedione ISEs. That is, these non-thiazolidinedione ISEs have similar thiazolidinedione ISE biologic activity (e.g., lowering of blood glucose, insulin levels, and lipid levels) and recognize the same or related putative cell receptors. As used herein, the term "immunogen" refers to any substance that is capable of eliciting an immune response when coupled, preferably covalently, to a thiazolidinedione ISE or a fragment of a thiazolidinedione ISE.

Labeled Thiazolidinedione ISE Conjugates for Antibody Capture and Competition Assays The method of the present invention can be employed to measure or detect the effect of known and unknown thiazolidinedione ISEs and non-thiazolidinedione ISEs. The method of the present invention can also be used to identify antibodies with high binding affinity for thiazolidinedione ISEs. In each method, a labeled protein is covalently coupled to a thiazolidinedione ISE. Preferably, the protein is a fluorescent compound.

Any number of fluorescent labeling compounds can be employed in the present invention. Useful fluorescent labels include, but are not limited to, fluorescein, rhodamine, phycobiliproteins, and derivatives thereof. Preferred fluorescent compounds include the phycobiliproteins, e.g., β-phycoerythrin, R-phycoerythrin, and allophycocyanin.

The fluorescent label will be coupled to the thiazolidinedione ISE to form a conjugate by an appropriate linkage group or covalent attachment, depending on the specific fluorescent label and thiazolidinedione ISE to be employed. A preferred conjugate is thiazolidinedione ISE covalently bound to a fluorescent phycobiliprotein. By way of nonlimiting example, in the assays described herein, a CS-045 bPE or LY 301318 bPE conjugate may be used.

Antibodies

The non-thiazolidinedione ISE screening and detection assays of the present invention employ a first antibody to a thiazolidinedione ISE compound. The first antibody can be any thiazolidinedione ISE-specific polyclonal or monoclonal anti-thiazolidinedione ISE antibody. For example, any number of antibodies derived from a mammalian source can be used, including mouse, rabbit, human, and chimeric antibodies. A preferred first antibody is a murine monoclonal anti-thiazolidinedione ISE antibody. More particularly, a monoclonal antibody produced by hybridoma cell line 13E3 (ATCC Deposit No. HB 11359) is preferred. This hybridoma was deposited on May 25, 1993 with the American Type Culture Collection (ATCC), Rockville, Md., 20852, U.S.A.

The second antibody can be any acceptable anti-species immunoglobulin antibody that can capture the first antibody thiazolidinedione or non-thiazolidinedione ISE complex and the first antibody fluorescent labeled conjugate complex in a sample. For example, goat anti-species IgG or IgM can be employed. For use in the invention, the second antibody is conjugated to an appropriate substrate, such as latex beads of micron dimension, polystyrene, or the like.

The present invention further includes anti-idiotypic antibodies that bind to the same site on an antibody to a thiazolidinedione ISE as a thiazolidinedione ISE. These anti-idiotypic antibodies can be used to identify, isolate, and characterize thiazolidinedione ISE receptor(s). Preferred anti-idiotypic antibodies are those which bind the thiazolidinedione ISE binding site on antibody 13E3. Two such antibodies are anti-idiotypic antibodies 2E5 and 7E7, deposited with the ATCC as Deposit Nos. HB 11360 and HB 11358, respectively.

Procedures

Screening for Novel Non-Thiazolidinedione ISEs

Those of skill in the art will understand that the present invention can be employed to screen for novel non-thiazolidinedione ISEs. The present method can be used to qualitatively or quantitatively detect or determine non-thiazolidinedione ISEs in a sample.

In the present method, a sample containing a non-thiazolidinedione compound suspected to have thiazolidinedione ISE activity is incubated with a first antibody to a thiazolidinedione ISE and a substrate-bound second antibody conjugate to form a complex of first antibody with the non-thiazolidinedione ISE which is bound to the second antibody conjugate. After incubation for a sufficient period of time, a fluorescent labeled thiazolidinedione ISE conjugate is added to perform a competitive binding assay with any non-thiazolidinedione ISE compound in the sample. After incubation of the sample, the amount of unbound fluorescent conjugate or fluorescent labeled thiazolidinedione ISE bound to substrate by the first and second antibodies is measured.

In the present method, the epifluorescence of bound fluorescent conjugate is measured in a fluorescence analyzer at one or more predetermined signal wavelengths. Referenced wavelengths are established to correct for well-to-well variations in the manner similar to that described in Taber et al., *Clinical Chem.*, 37(2):254 (1991), incorporated by reference herein.

Thiazolidinedione Antibody Selection

A further example of the applicability of the present invention is as a method for selecting an antibody with specific binding affinity to a thiazolidinedione ISE compound. In this use, the antibody is selected by first administering a thiazolidinedione ISE immunogen to a mammal such as a rabbit, goat, mouse, or the like. Spleen cells exhibiting an elevated antibody titer to the thiazolidinedione ISE immunogen are harvested from the immunized mammal. Hybridomas of spleen cells and mouse myeloma cells are produced utilizing the technique of Galfre and Milstein, *Meth. Enzymol.*, 73, 3–46 (1981), incorporated by reference herein. After fusion, cells are distributed into plates and a hybridoma medium is screened for monoclonal antibody binding to the thiazolidinedione ISE employed in the above-described immunogen using a labeled antibody capture method, preferably the fluorescent antibody capture method. Monoclonal antibodies are screened for their ability to bind a plurality of chosen thiazolidinedione ISEs. Such thiazolidinedione ISEs are exemplified by LY 282449, CS-045, and ciglitazone. Monoclonal antibodies exhibiting high binding affinity to each of the chosen thiazolidinedione ISEs employed in screening can thus be used for further detection and monitoring assays of the type described herein.
Measurement of Plasma Levels of Thiazolidinedione or Non-thiazolidinedione Insulin Sensitivity Enhancers

A fluorescent antibody competition assay can be employed to test thiazolidinedione and non-thiazolidinedione ISEs for type II anti-diabetic activity. Such an assay is conducted by first obtaining a plasma sample from an animal or a patient who has received a predetermined amount of the thiazolidinedione or non-thiazolidinedione ISE compound. The fluorescence immunoassay is then conducted employing a thiazolidinedione ISE-specific monoclonal antibody, such as the antibody produced by cell line 13E3 or other antibodies produced by the method described above. The amount of labeled thiazolidinedione ISE first antibody complex, which is bound to the second antibody conjugate, is then analyzed to determine the amount of anti-diabetic thiazolidinedione ISE/non-thiazolidinedione ISE activity in the sample. Thus, the fluorescent-labeled thiazolidinedione ISE conjugate and monoclonal antibody to thiazolidinedione ISE can be used in an assay to determine buffer and tissue concentrations of immunologically positive compounds by those of skill in the art.

Example I

Immunogens and Antibodies

Preparation of Mouse Monoclonal Anti-CS-045 Antibodies

Figure 1:
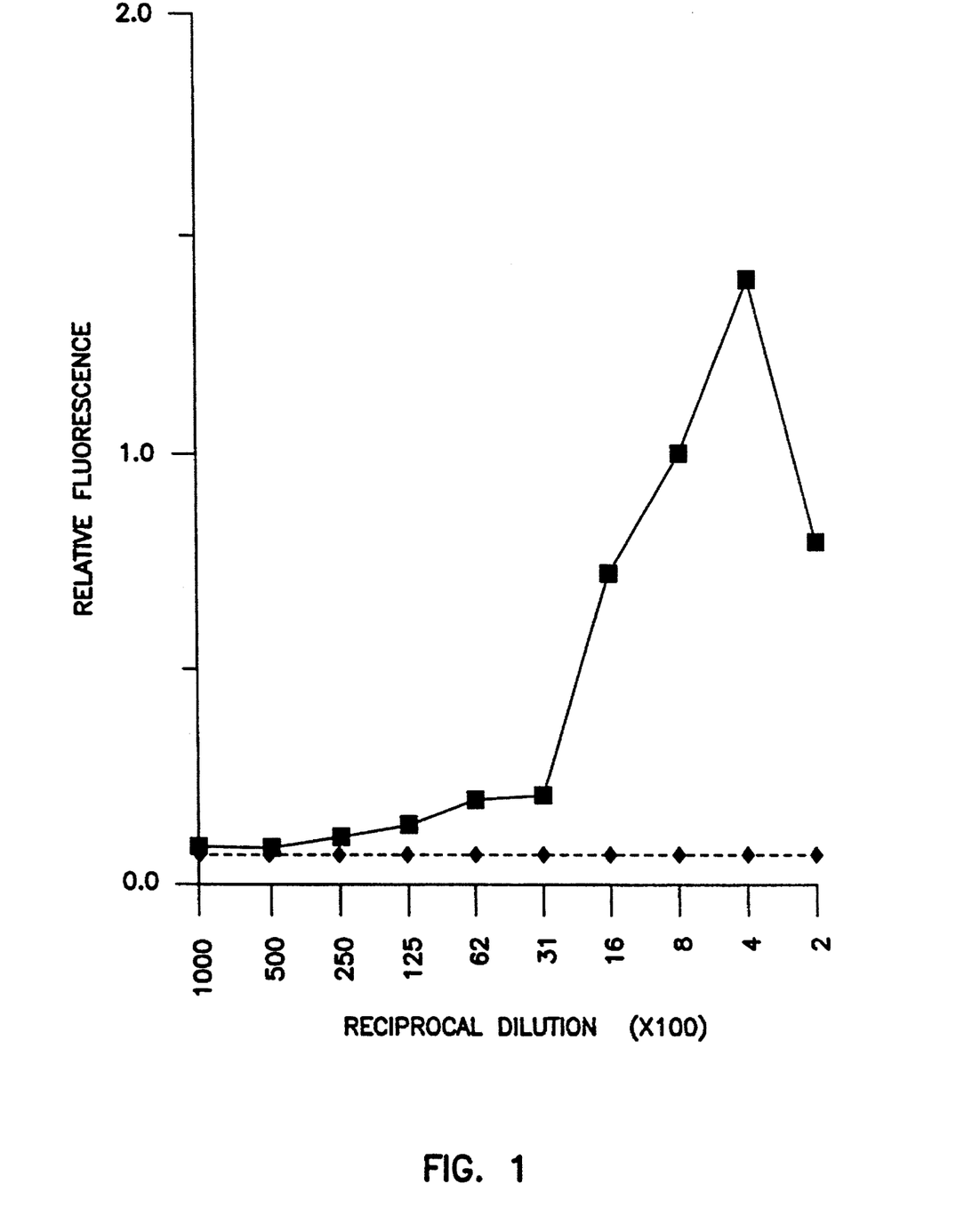
FIG. 1 shows the difference in titers between a pre-immune serum and a positive immune serum based on relative fluorescence [mouse anti-serum (■); pre-immune mouse serum (♦)].

As seen below, in order to render thiazolidinedione ISE CS-045 immunogenic, it (44 mg CS-045) was first reacted with succinic anhydride (100 mg) in pyridine for approximately 6 hours at 85° C. to produce a succinyl CS-045 conjugate, which then was covalently coupled to PPD (purified protein derivative from tuberculin bacillus protein) (Lederle-Praxis Biological, Pearl River, N.Y.). As is shown in FIG. 1, covalent coupling of succinyl CS-045 to PPD to produce the CS-045 PPD immunogen was accomplished using a water soluble carbodiimide procedure, namely 1-ethyl-3(dimethylaminopropyl) carbodiimide (EDC) enhanced by sulfo-NHS (Pierce Chemical, Rockford, Ill.). This procedure is essentially described in Taber et al., *Clinical Chemistry*, 37(2):254 (1991), incorporated by reference herein.

SYNTHESIS OF CS-045-PPD IMMUNOGEN

Prior to immunization of mice with CS-045 PPD immunogen, Balb/c mice (Charles River Labs, Wilmington, Mass.) were primed with BCG (a mycobacterium). They then were immunized and boosted with subcutaneous injections of 25 μg CS-045 PPD immunogen emulsified with Freund's incomplete adjuvant (400 μl/mouse). Immunized and boosted mice were bled and serum antibody titers determined using the CS-045 bPE (beta phycoerythrin) fluorogen and the fluorescent antibody capture assay described below. An example of the difference in titers between pre-immune serum and a positive immune serum is shown in FIG. 1.

Mice with an adequate serum titer (greater than 1:25,000) were given a single intraperitoneal dose of CS-045 PPD immunogen (50 μg). Three days later, mice were sacrificed and spleen cells were harvested and fused with mouse myeloma cells by the technique of Galfre and Milstein, Id. After fusion, cells were distributed into 96-well plates and approximately 1200 hybridomas were selected with HAT medium.

All hybridoma media were screened for monoclonal anti-CS-045 antibodies on day 17 after fusion. The fluorescent antibody capture method was used and approximately 60 monoclonal antibodies were positive for binding of the CS-045 bPE fluorogen. Among these positive monoclonal antibodies, approximately 6 had binding affinity for 3 tested thiazolidinedione ISEs—LY 282449, CS-045, and ciglitazone. Fifty percent binding inhibitory concentrations ($IC_{50}$) were determined and data from 4 monoclonal antibodies are shown in Table 1 below. Among these 4 antibodies, 13E3 was selected for high-volume screening based on the following criteria: (1) high binding affinity for all three thiazolidinedione ISEs; and (2) higher binding affinity (lower $IC_{50}$) for the more biologically potent ISE (LY 282449) than for the less biologically potent ISE (ciglitazone).

TABLE 1

| Compound | IC50 (nM) Determined with MoAb | | | |
|---|---|---|---|---|
| | 13E3 | 8F1 | 10E1 | 8D6 |
| LY 282449 | 520 | 4,980 | 1,410 | 4,760 |
| Ciglitazone | 1,160 | 12,260 | 989 | 125 |
| CS-045 | 200 | 1,150 | 30 | 77 |

Preparation of Rabbit Anti-LY 301318 Antibodies

As shown below, LY 301318 (150 mg) was reacted with succinic anhydride (250 mg) in pyridine for approximately 6 hours at approximately 85° C. to produce the succinyl LY 301318 conjugate shown below. This succinyl LY 301318 conjugate was then covalently coupled to PPD to form a LY 301318 PPD immunogen using the same water soluble carbodiimide procedure described above. Approximately 200 μg of LY 301318 PPD immunogen emulsified in Freund's incomplete adjuvant was injected into New Zealand white rabbits that were pre-primed with BCG. Multiple boosters were administered in Freund's incomplete adjuvant. Rabbits subsequently were bled and positive antisera determined using an LY 301318 bPE fluorogen and the fluorescent antibody capture method described below.

LY 282449

SYNTHESIS OF LY301318 IMMUNOGEN

-continued
SYNTHESIS OF LY301318 IMMUNOGEN

LY301318-PPD Immunogen

Preparation of Anti-idiotype Antibodies to Mouse Monoclonal Antibody 13E3

Monoclonal antibody 13E3 was cleaved into F(ab')$_2$ fragments by incubation for approximately 8 hours at approximately 37° C. with pepsin at approximately pH 3.6. These F(ab')$_2$ fragments were purified using a protein A column and dialyzed to remove F(c') fragments [Tassi et al., *Immunology Letters*, 27:39–44 (1991)]. Purified, dialyzed monoclonal antibody 13E3 F(ab')$_2$ fragments were injected into Balb/c mice at a dose of 100 µg in Freund's complete adjuvant to make anti-idiotypic antibodies. Two boosters in incomplete Freund's adjuvant were administered.

Figure 2:
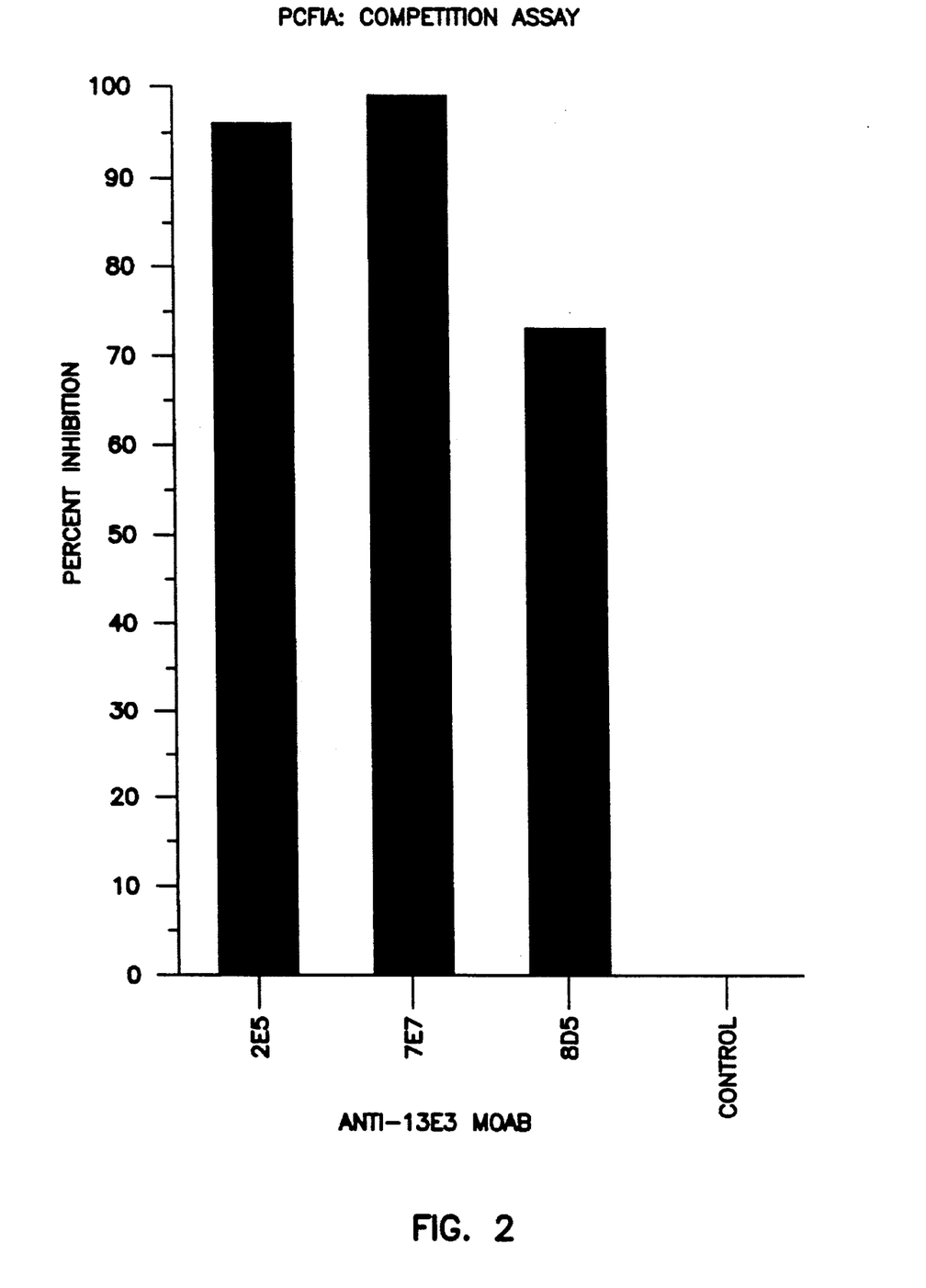
FIG. 2 shows a PCFIA (Particle Concentration Fluorescence Immuno Assay) competition assay for anti-idiotype antibodies to monoclonal antibody 13E3.

Mice were bled and positive antisera were determined using the fluorescent antibody competition assay with monoclonal antibody 13E3 and the CS-045 bPE fluorogen described below. Upon determination of adequate titers, mice were sacrificed and hybridomas were produced as described above. Hybridoma media were screened in the fluorescent antibody capture assay and results from 3 positive media are shown in FIG. 2. Thus, these anti-idiotypic antibodies either bind at the same site or cover the binding site for the CS-045 fluorogen on 13E3.

Figure 3:
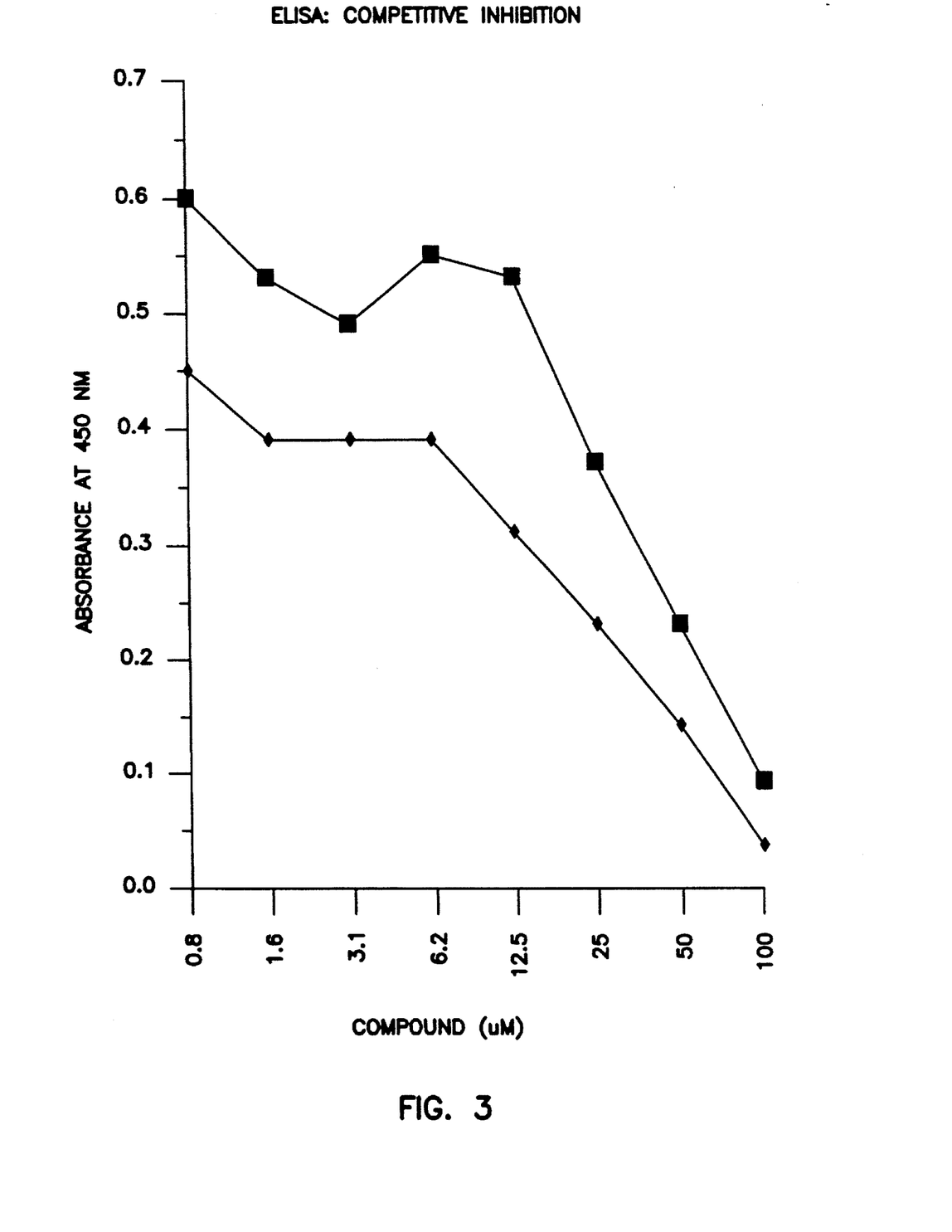
FIG. 3 shows an ELISA (Enzyme Linked Immuno Sorbent Assay) competitive inhibition assay between CS-045 and anti-idiotype antibodies 2E5 (■) and 7E7 (◆).

To test whether or not CS-045 could, in turn, displace these anti-idiotypic antibodies, 0.3 µg/well of 13E3 F(ab')$_2$ fragments were coated onto microtiter plates and blocked with 1% BLOTTO (non-fat dry milk). Between 0–200 µM of CS-045 was added to duplicate wells. After approximately two hours at room temperature, wells were washed with BLOTTO and 500 ng of anti-idiotypic antibody 2E5 or 7E7 was added for approximately 1 hour. Goat anti-mouse (F$_c$-specific) conjugated with horseradish peroxidase was added and, after 30 minutes, washed 3 times with BLOTTO. A peroxidase substrate, tetramethylbenzidine (Kirkegaard and Perry Laboratories, Gaithersberg, Md.) was added and color was developed for approximately 30 minutes at room temperature. Data from this assay demonstrate that CS-045 can displace two anti-idiotypic antibodies and are shown in FIG. 3. These two anti-idiotypic antibodies, 2E5 and 7E7, appear either to bind to the CS-045 site or to cover the CS-045 recognition site on antibody 13E3.

Example 2

Fluorescent Labeled Thiazolidinedione ISE and Antibody Capture Assay

Using the same carbodiimide method as shown in Example 1, succinyl CS-045 conjugate or succinyl LY 301318 is covalently coupled with the fluorescent protein, beta phycoerythrin (bPE) (Molecular Probes, Inc., Eugene, Oreg.).

To make the succinyl CS-045 conjugate of β-phycoerythrin, first 44 mg of CS-045 was reacted for 5 hours at room temperature with 20 mg succinic anhydride in pyridine. Then 4 mg of the resulting succinyl CS-045 was reacted overnight at 4° C. with 2 mg EDC and 1.2 mg N-hydroxysuccinimide to produce CS-045 succinimide. Forty micrograms of this CS-045 succinimide was reacted for 4 hours at room temperature with 500 µg β-phycoerythrin. The final succinyl CS-045 conjugate of β-phycoerythrin was precipitated with 60% final (w/v) saturated ammonium sulfate and resuspended in phosphate buffered saline.

To make the succinyl LY 301318 conjugate of β-phycoerythrin, first 150 mg LY 301318 was reacted for 2 hours at 60° C. with 250 mg succinic anhydride in pyridine. Then 5 mg of the resulting succinyl LY 301318 was reacted 6 hours at room temperature with 4 mg EDC and 2.2 mg N-hydroxysuccinimide to produce LY 301318 succinimide. Fifty micrograms of this LY 301318 succinimide was reacted for 4 hours at room temperature with 2.5 mg β-phycoerythrin. The final succinyl LY 301318 conjugate of β-phycoerythrin was precipitated with 60% final (w/v) saturated ammonium sulfate and resuspended in phosphate buffered saline.

These CS-045 bPE or LY 301318 bPE were used as the fluorogens both in fluorescent antibody capture assays and in fluorescent competition binding assays.

In fluorescent antibody capture assays, the appropriate fluorogen (20 βl/well; 1:200 dilution) was incubated with undiluted sera or hybridoma media (20 βl/well) in the presence of goat anti-mouse IgG coupled to 0.9 βm polystyrene particles (IDEXX, Westbrook, Me.) (20 βl/well; 1:2 dilution). Incubations were done in 96-well Pandex plates and the reaction mixture was separated from particles by vacuum filtration using a vacuum of 25 inches of mercury applied to the vacuum port on Pandex plates. Polystyrene particles retained on the Pandex filters were then washed and solid-phase fluorescence was determined at 575 nm using 540 nm illumination. Fluorescence reference particles (IDEXX) were also added to each well to minimize well-to-well variation in filtration, and reference fluorescence was determined at 620 nm using 590 nm illumination. Assay buffers typically contained bovine serum albumin (Sigma, St. Louis, Mo.) at 0.2% (for assays containing murine monoclonal antibodies or hybridoma media) or 0.5% BLOTTO (for assays containing rabbit antibodies). Specific relative fluorescence was calculated from the fluorescent ratio of 575 nm/620 nm.

Example 3

Fluorescent Antibody Competition Assay

Serial dilutions of test compound, fermentation broth, or tissue containing test compound or putative anti-idiotype culture supernatant (20 µl/well) were incubated 20 minutes in 96-well Pandex plates with the appropriate antibody (20 µl/well; 1 µg/ml) plus either goat anti-mouse IgG Latex beads or goat anti-rabbit IgG linked to polystyrene beads (IDEXX) (20 µl/well; 1:2 dilution). Fluorescent reference particles (IDEXX) were included in all assays to minimize well-to-well variation in filtration. Fluorescent CS-045 bPE or LY 301318 bPE (20 µl/well; 1:2,000 dilution) was then added to the wells. Incubations were terminated after 20 minutes by vacuum filtration and the polystyrene particles retained on the Pandex filters were then washed twice with TBS-A buffer (described below) and solid phase fluorescence determined as described above.

Assay buffers typically contained bovine serum albumin (Sigma) at 0.2% (for monoclonal antibody assays) or 0.5% BLOTTO (non-fat dry milk for rabbit antibody assays). Percent inhibition of binding in test incubations was calculated in relationship to binding in control incubations in which no test compound was added using the following formula: % inhibition=[1-(fluorescence at 575/620 nm in test incubations divided by fluorescence at 575/620 nm in control incubations)×100)]. Concentrations of test compound in fermentation broth or plasma was calculated by interpolation from a standard curve generated with known concentrations of the appropriate compound as described in Taber et al., *Clinical Chemistry*, 37(2):254 (1991).

Example 4

High-volume Screening for Novel, Non-thiazolidinedione ISEs Using a Fluorescent Antibody Competition Assay The fluorescent antibody competition assay for high-volume screening was adapted as described below. Goat anti-mouse particles (1:2 dilution), fluorescent reference particles (dilution was optimized for each lot), and monoclonal antibody 13E3 (1 µg/ml) were premixed in TBS-A reaction buffer (0.02M Tris, 0.15M NaCl, 0.2% bovine serum albumin, 0.01% thimerosal, pH 7.5) and 40 µls was added to each well of the Pandex plate. Synthetic organic compounds (dissolved at 5 mg/ml DMSO and then diluted in TBS-A reaction buffer to 2 µg/ml) or 1:40 dilutions of fermentation broths were added to appropriate wells (20 µl/well) and incubated for approximately 20 minutes at room temperature. To each well was next added 20 µl of CS-045 bPE fluorogen; this final mixture was again incubated for approximately 20 minutes at room temperature in the dark. Wells were then aspirated by vacuum filtration and washed twice with TBS-A reaction buffer, and surface fluorescence was read at 545/575 nm and 590/620 nm using the Screen Machine (IDEXX Laboratories, Westbrook, Me.). Each Pandex plate contained both a negative control (only reaction buffer) and a positive control (LY 282449).

Final concentrations of synthetic organic compounds in high-volume screens was approximately 2 µg/ml and final concentrations of filtered fermentation broths were 1:40 (v/v). Wells that produced greater than 50% inhibition of binding of CS-045 bPE on both the initial screening and on retesting were considered positives. The positive hit rate for synthetic organic compounds was approximately 0.20%; false positives occurred at a rate of approximately 0.05%. The positive hit rate for fermentation broths was approximately 0.19%; the combined rate of broths that failed to referment or that were false positives occurred at a rate of approximately 0.12%. For both synthetic organic compounds and fermentation broths, the primary reason that compounds were picked up as false positives was that they quenched fluorescence at 575 nm and/or auto fluoresced at 620 nm. This problem was eliminated by inspection of data from each channel. An example of data from each channel of a true positive and a false positive is shown in Table 2 below.

TABLE 2

| LY Compd. | Conc. (µM) | Relative Fluoresc./Channel | |
|---|---|---|---|
| | | Sample 545/575 nm | Reference 590/620 nm |
| None | — | 14,000 | 6,500 |
| 116196 | 4.0 | 360 | 6,500 |
| 028447* | 4.0 | 4,200 | 27,000 |

*False Positive

Example 5

Novel Non-thiazolidinedione Compounds From High-Volume Screen

Tables 3A and 3B contain a list of the novel synthetic organic structures and Table 4 contains a list of the fermentation broths that were positive in this screen. When approximately 70 compounds were selected for structural similarity with LY 116196 and submitted to the high-volume screen, the positive hit rate increased more than 10-fold to 2.7%. In addition to non-thiazolidinediones, 10 thiazolidinediones also were positive in the high-volume screen and had $IC_{50}$s between 60 and 2,000 nM.

In order to determine if any of these novel, non-thiazolidinedione structures had anti-diabetic activity, LY 116196 was administered subcutaneously for three days to female Avy/a mice, which had been made diabetic by implantation of dexamethasone pellets. These dexamethasone-treated mice are characterized by both hyperglycemia and hyperinsulinemia and are models of type II diabetes. Sulfonylureas and other insulin secretagogues have little, if any, effect on blood glucose concentrations in this insulin-resistant animal model. However, several thiazolidinedione ISEs have been found that normalize glucose levels. As shown in FIG. 4, LY 116196 also effectively lowered fed blood glucose in this animal model. Thus, this high-volume screen has detected a novel, anti-diabetic compound, LY 116196.

| NON-THIAZOLIDINDIONE HITS FROM HIGH-VOLUME SCREEN | | | |
|---|---|---|---|
| LY NUMBER | % INHIB. IN SCREEN | IC50 (NM) | CHEMICAL STRUCTURE |
| 044047 | 61 | 4,000 |  |

-continued

NON-THIAZOLIDINDIONE HITS FROM HIGH-VOLUME SCREEN

| LY NUMBER | % INHIB. IN SCREEN | IC50 (NM) | CHEMICAL STRUCTURE |
|---|---|---|---|
| 047310 | 60 | 5,000 |  |
| 099238 | 87 | 2,000 |  |
| 116196 | 105 | 60 |  |
| 181036 | 90 | 2,000 |  |
| 222072 | 101 | 8,000 |  |
| 281809 | 89 | 2,000 |  |
| 283909 | 70 | N.D. |  |
| 305329 | 53 | 3,600 |  |
| 305334 | 89 | 250 |  |

-continued

| | | | NON-THIAZOLIDINDIONE HITS FROM HIGH-VOLUME SCREEN |
|---|---|---|---|
| LY NUMBER | % INHIB. IN SCREEN | IC50 (NM) | CHEMICAL STRUCTURE |
| 296345 | 94 | 250 | |
| 301563 | 88 | 250 | |
| 800663 | 65 | 8,000 | |
| 820960 | 55 | 4,000 | |
| 825447 | 56 | 10,000 | |

TABLE 4

| Cassette Number | Type of Organism | IC50 (fold dilution) |
|---|---|---|
| A37979 | Mold | 30 |
| A38377 | Mold | 30 |
| A92501 | Actinomyces | 40 |
| A92565 | Actinomyces | 30 |
| A92513 | Actinomyces | 40 |

Example 6

Measurement of Plasma Levels of LY 116196 with the Fluorescent Antibody Competition Assay In the same experiment described in FIG. 4, plasma was prepared from tail blood drawn at 1, 3, 6, and 24 hours after the third subcutaneous injection of LY 116196. Plasma concentrations of LY 116196 (shown in Table 5) were determined directly by the fluorescent antibody competition assay using standards of LY 116196 diluted in TBS-A buffer containing 10% (v/v) normal mouse plasma. This method also has been used to measure blood concentrations of several compounds recognized by monoclonal antibody 13E3 and/or other antibodies produced by the methods described above. Thus, these reagents appear to have general utility for determining buffer and tissue concentrations of immunologically positive compounds.

TABLE 5

| | Plasma Concentration of LY 116196 ($\mu$mol/l) | | | |
|---|---|---|---|---|
| | Number of Hours After the Third Subcutaneous Injection | | | |
| Dose | 1 hr | 3 hr | 6 hr | 24 hr |
| Control | 0 | 0 | 0 | 0 |
| 30 mg | 25.0 ± 11.0 | 0.320 ± 0.20 | 0.104 ± 0.052 | 0 |
| 100 mg | 83.3 ± 8.0 | 6.0 ± 1.6 | 0.268 ± 0.088 | 0 |
| 300 mg | 528.0 ± 72.0 | 24.0 ± 5.5 | 6.4 ± 3.0 | 0.452 ± 0.022 |

What is claimed is:

1. A method for using antibodies to detect non-thiazolidinedione and thiazolidinedione insulin sensitivity enhancer compounds in a sample, comprising the steps of:

(a) providing a sample containing a non-thiazolidinedione or thiazolidinedione compound suspected to have thiazolidinedione insulin sensitivity enhancer activity;

(b) incubating said sample with a first antibody to a thiazolidinedione insulin sensitivity enhancer and a substrate-bound second antibody conjugate to form a complex of first antibody with said non-thiazolidinedione or thiazolidinedione insulin sensitivity enhancer, said first antibody of said complex bound to said second antibody of said conjugate, said first antibody having an IC50 of 200 nmol/l or less for thiazolidinedione ISE CS-045, an IC50 of 520 nmol/l or less for thiazolidinedione ISE LY 282449, and an IC50 of 1160 nmol/l or less for ciglitazone, said first antibody being a monoclonal antibody produced by hybridoma cell line 13E3 (ATCC Deposit No. HB 11359);

(c) adding a labeled thiazolidinedione insulin sensitivity enhancer compound conjugate to said sample, said labeled thiazolidinedione insulin sensitivity enhancer conjugate forming a complex with said first antibody which is bound with said second antibody conjugate; and (d) measuring the amount of labeled thiazolidinedione insulin sensitivity enhancer first antibody complex bound with second antibody conjugate to determine the presence of a non-thiazolidinedione or thiazolidinedione insulin sensitivity enhancer in said sample.

2. The method of claim 1 wherein said labeled thiazolidinedione insulin sensitivity enhancer is a conjugate of CS-045 or LY 301318 with a fluorescent protein compound.

3. The method of claim 1 wherein said labeled thiazolidinedione insulin enhancer is a conjugate of CS-045 or LY 301318 with β-phycoerythrin.

4. A fluorescent immunoassay for detecting non-thiazolidinedione or thiazolidinedione insulin sensitivity enhancer compounds in a sample that exhibits thiazolidinedione insulin sensitivity enhancer compound immunological activity, comprising the steps of:

(a) providing a sample containing a non-thiazolidinedione or thiazolidinedione compound suspected to have thiazolidinedione insulin sensitivity enhancer activity;

(b) incubating said sample with a first anti-thiazolidinedione ISE antibody having the characteristics of an antibody produced by cell line 13E3 (ATCC Deposit No. HB 11359), which binds to thiazolidinedione insulin sensitivity enhancer compounds and a substrate-bound second antibody conjugate to form a complex of first antibody with said non-thiazolidinedione or thiazolidinedione insulin sensitivity enhancer, said first antibody of said complex bound to said second antibody of said conjugate;

(c) adding a fluorescent-labeled thiazolidinedione insulin sensitivity enhancer compound to said sample, said labeled thiazolidinedione insulin sensitivity enhancer forming a complex with said first antibody, which is bound to said second antibody conjugate; and (d) measuring the amount of fluorescent-labeled thiazolidinedione insulin sensitivity enhancer first antibody complex bound with second antibody conjugate to determine the presence of a non-thiazolidinedione or thiazolidinedione insulin sensitivity enhancer in said sample.

5. A method for monitoring blood levels of a type II anti-diabetic thiazolidinedione and/or non-thiazolidinedione insulin sensitivity enhancer compound comprising the steps of:

(a) obtaining a plasma sample from an animal or a patient having received a predetermined amount of said thiazolidinedione or non-thiazolidinedione insulin enhancer compound;

(b) incubating said sample with a first antibody to a thiazolidinedione insulin sensitivity enhancer and a substrate-bound second antibody conjugate to form a complex of first antibody and said thiazolidinedione or non-thiazolidinedione insulin enhancer, said first antibody of said complex bound to said second antibody of said conjugate, said first antibody having an IC50 of 200 nmol/l or less for thiazolidinedione ISE CS-045, an IC50 of 520 nmol/l or less for thiazolidinedione ISE LY 282449, and an IC50 of 1160 nmol/l or less for ciglitazone, said first antibody being a monoclonal antibody produced by hybridoma cell line 13E3 (ATCC Deposit No. HB 11359);

(c) adding a labeled thiazolidinedione insulin sensitivity enhancer compound to said sample, said labeled thiazolidinedione insulin sensitivity enhancer forming a complex with said first antibody which is bound to said second antibody conjugate; and (d) measuring the amount of labeled thiazolidinedione insulin sensitivity enhancer first antibody complex which is bound to said second antibody conjugate and using a standard curve generated with known amounts of the administered compound to determine the amount of said anti-diabetic thiazolidinedione insulin sensitivity enhancer or non-thiazolidinedione insulin sensitivity enhancer in said sample.

6. The method of claim 5 wherein said non-thiazolidinedione insulin sensitivity enhancer compound is LY 116196.

7. A monoclonal antibody produced by hybridoma cell line 13E3 having specific binding affinity for thiazolidinedione and non-thiazolidinedione insulin sensitivity enhancer compounds and the identifying characteristics of ATCC Deposit No. HB 11359.

* * * * *

UNITED STATES PATENT AND TRADEMARK OFFICE
CERTIFICATE OF CORRECTION

PATENT NO. : 5,466,610

DATED : November 14, 1995

INVENTOR(S) : Stuart W. Bright et al.

Figure 4A:
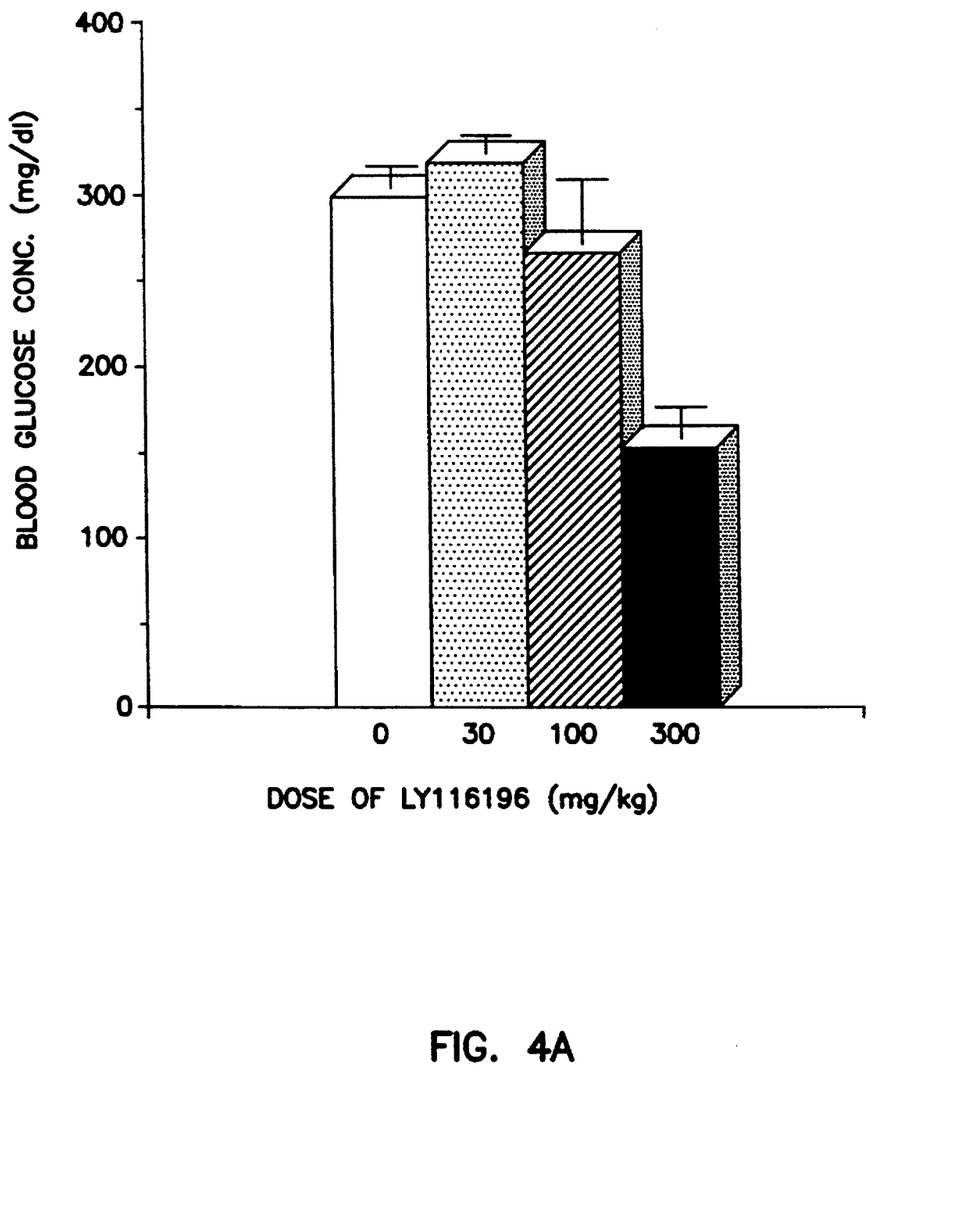
FIG. 4 shows blood glucose concentration in diabetic female (Avy/a) mice receiving the non-thiazolidinedione anti-diabetic compound LY 116196.
Figure 4B:
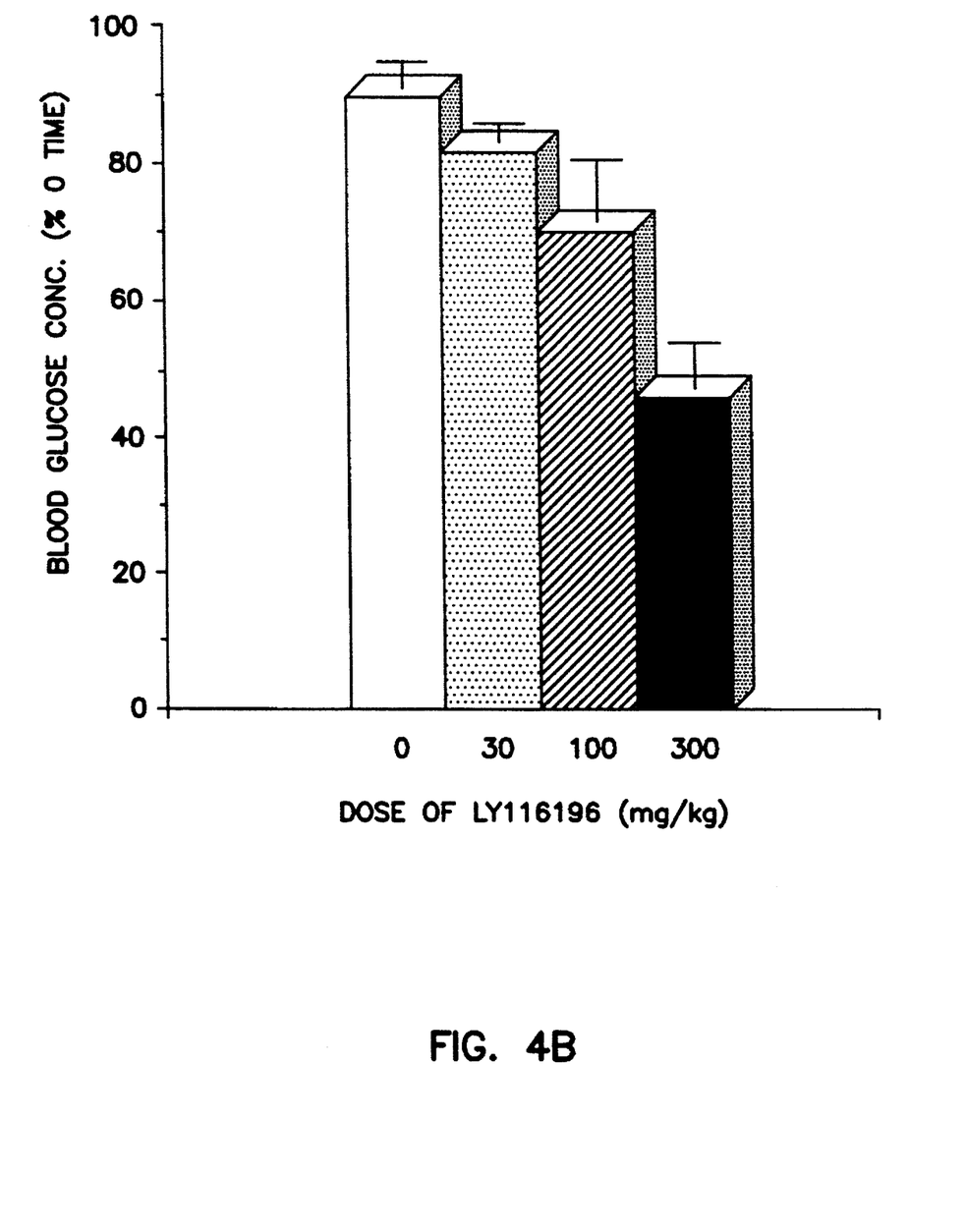

It is certified that error appears in the above-indentified patent and that said Letters Patent is hereby corrected as shown below:

At column 3, line 5, for "FIG. 4" read --FIGS. 4A and 4B--

At column 10, line 37, for "(20 $\beta$l/well;" read --(20 $\mu$l/well;--

At column 10, line 38, for "(20 $\beta$l/well)" read --(20 $\mu$l/well)--

At column 10, line 39, for "0.9 $\beta$m" read --0.9 $\mu$m--

At column 10, line 40, for "(20 $\beta$l/well;" read --(20 $\mu$l/well;--

At column 12, line 52, for "FIG. 4" read --FIGS. 4A and 4B--

UNITED STATES PATENT AND TRADEMARK OFFICE
CERTIFICATE OF CORRECTION

PATENT NO. : 5,466,610

DATED : November 14, 1995

INVENTOR(S) : Stuart W. Bright et al.

It is certified that error appears in the above-indentified patent and that said Letters Patent is hereby corrected as shown below:

At column 15, line 61, for "FIG. 4" read --FIGS. 4A and 4B--

At column 16, in the first chemical structure (LY 296345), for "P=O" read --P:O--

Signed and Sealed this

Twenty-eighth Day of May, 1996

Attest:

BRUCE LEHMAN

*Attesting Officer*    *Commissioner of Patents and Trademarks*